United States Patent [19]
Türeci et al.

[11] Patent Number: 5,888,751
[45] Date of Patent: Mar. 30, 1999

[54] METHOD FOR DIAGNOSIS AND TREATING CANCERS, AND METHODS FOR IDENTIFYING PATHOGENIC MARKERS IN A SAMPLE OF NORMAL CELLS

[75] Inventors: Özlem Türeci; Ugur Sahin; Michael Pfreundschuh, all of Homburg/Saar, Germany

[73] Assignee: Ludwig Institute for Cancer Research, New York, N.Y.

[21] Appl. No.: 892,702

[22] Filed: Jul. 15, 1997

[51] Int. Cl.⁶ ............................. G01N 33/574; C12Q 1/68
[52] U.S. Cl. ................. 438/7.23; 435/6; 436/64; 436/813
[58] Field of Search ................ 435/7.23, 6; 436/64, 436/813

[56] References Cited

PUBLICATIONS

Tureci et al., *PNAS*, vol. 95, No. 9, pp. 5211–5216, Apr. 28, 1998.

Heyting et al., "Synaptonemal Complex Proteins", Genome 31: 81–87 (1989).

Meuwissen et al., "A coiled coil related protein specific for synapsed regions of meiotic prophase chromosome", EMBO J 11 (13:5091–5100 (1992).

Sage et al., cDNA sequence of the murine synaptonemal complex protein 1 (SCP1) Biochimica Biophipica Acta 1263: 258–260 (1995).

Meuwissen et al., "Human Synaptonemal Complex Protein 1 (SCP1) : Isolation and Characterization of the cDNA and Chromosomal Localization of the Gene", Genomics 39: 377–384 (1996).

*Primary Examiner*—Toni R. Scheiner
*Attorney, Agent, or Firm*—Fulbright & Jaworski, LLP.

[57] ABSTRACT

The invention involves the recognition of a previously identified protein, SCP-1, as a marker for cell transformation. Diagnostic and therapeutic uses of this protein and related molecules are taught. Also disclosed is a method for identifying substances which are immunoreactive and indicative of pathological conditions, using normal cells as source material.

21 Claims, No Drawings

METHOD FOR DIAGNOSIS AND TREATING CANCERS, AND METHODS FOR IDENTIFYING PATHOGENIC MARKERS IN A SAMPLE OF NORMAL CELLS

FIELD OF THE INVENTION

The invention relates to the identification of a molecule or a marker for transformed cells, such as cancer cells. It also relates to a method for identifying molecules associated with pathological conditions, such as cancer.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding nucleic acid molecule to express the desired protein molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of cytolytic T cell lines (CTLs) proliferation tumor necrosis factor (TNF) release, and lysis of target cells, measurable in an MTT assay, or a $^{51}Cr$ release assay.

These two approaches to the molecular definition of antigens have the following disadvantages: first, they are enormously cumbersome, time-consuming and expensive; second, they depend on the establishment of CTLs with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Richard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies supra described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, thus precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. patent application Ser. No. 08/580,980, now U.S. Pat. No. 5,698,396 and application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has been applied to esophageal cancer samples, and an esophageal cancer associated antigen has now been identified, and its encoding nucleic acid molecule isolated and cloned, as per U.S. patent application Ser. No. 08/725,182, filed Oct. 3, 1996, incorporated by reference herein.

The relationship between some of the tumor associated genes and a triad of genes, known as the SSX genes, is under investigation. See Sahin, et al., supra; and Tureci, et al., Cancer Res 56:4766–4772 (1996). One of these SSX genes, referred to as SSX2, was identified, at first, as one of two genes involved in a chromosomal translocation event (t(X; 18)(p 11.2; q 11.2)), which is present in 70% of synovial sarcomas. See Clark, et al., Nature Genetics 7:502–508 (1994); Crew et al., EMBO J 14:2333–2340 (1995). This gene was later found to be expressed in a number of tumor cells, and is now considered to be a tumor associated antigen referred to as HOM-MEL-40 by Tureci, et al, supra. Its expression to date has been observed in cancer cells, and normal testis only. This parallels other members of the "CT" family of tumor antigens, since they are expressed only in cancer and testis cells. Crew et al. also isolated and cloned the SSX1 gene, which has 89% nucleotide sequence homology with SSX2. See Crew et al., supra. Additional work directed to the identification of SSX genes has resulted in the identification of SSX3, as is described by DeLeeuw, et al., Cytogenet. Genet 73:179–183 (1996). The fact that SSX presentation parallels other CT antigens suggested to the inventors that other SSX genes might be isolated.

Application of a modification of the SEREX technology described supra has been used, together with other techniques, to clone two, additional SSX genes, referred to as SSX4 and SSX5 as well as an alternate splice variant of the SSX4 gene. This work is described in U.S. Ser. No. 08/851,138, filed May 5, 1997, incorporated by reference, as well as by Chen, et al., Proc. Natl. Acad. Sci USA 94: 1914–1918 (1997), also incorporated by reference.

The fact that many markers were found in both normal testis and tumor cells, but not other normal cells, suggested that further investigation in this area might uncover additional related molecules. The diversity of those discovered so far, however, did not provide any guidance as to the characteristics of the additional molecules which might be found.

Most of the work prior to the invention disclosed herein, used cDNA libraries obtained from cancer cells. As will be developed herein, it has now been shown that such molecules can also be determined using a non-transformed, or normal cell source for the cDNA libraries previously obtained from cancer cells. This is quite surprising, as it might well be assumed that tumor markers are expressed only in tumor cells. This has now been shown to not be the case. Exemplary of a normal cell library which can be used is a testis cell library screened against various serum samples, such as autologous serum.

The SEREX methodology, as described supra, has proven to be very useful in identifying molecules of interest. The inventors have found, however, that it is not an ideal method when short cDNA molecules are the ones of interest in a given library. One aspect of the invention described herein is a method for identifying short cDNA molecules which are of interest in connection with pathologies of the type discussed herein.

Synaptonemal complex protein 1 ("SCP1" hereafter) is a protein involved in the meiotic prophase of spermatocytes. The gene which encodes murine SCP1 has been mapped to chromosome 1p. 12-p.13. See Sage, et al, Biochem. Biophys. Acta 1263: 258–260 (1995) incorporated by reference. The human form of SCP1 has been reported to be expressed only in testis. See Meuwissen, et al, EMBO J 11:5091–5100 (1992), incorporated by reference.

Meuwissen et al, supra describe SCP1 protein as a major component of the synaptonemal complex, a tripartite, macromolecular assembly which is formed between homologous chromosomes during meiotic prophase. See Wettstein, et al, Annu. Rev. Genet 3:331–413 (1984); Heyting, et al, Genome 31:81–89 (1986). More details of the protein may be found e.g., in Meuwissen, et al, Genomics 37:101–106 (1997); Gillies, et al, Curr. Trac. Lab. Carlsberg 40:135–161 (1975); Schmekel, et al, Exp. Cell Res 226:20–30 (1996); Moses, et al, Symp. Soc. Exp. Biol. 38:245–270 (1984); Carpenter, Bioessays 6:232–236 (1987); Loidl, et al, Genome 33:759–778 (1990); Moens, Bioessays 16:101–106 (1994); Roeder, Trends Genet 6:385–389 (1990).

The location of the gene for SCP1 is different than that for all previously identified cancer testis antigens (CTAs), which map to the X chromosome.

It has been found, that SCP1 is expressed in tumor cells, especially in renal cell carcinomas, gliomas, and breast carcinomas, but not in normal cells except for testis. Hence, it serves as a CTA but differs in that it possesses strong expression not only in melanoma, but in those tumor types listed supra.

This is significant in terms of both diagnostic and therapeutic approaches to transformed cells, as will be seen from the disclosure which follows. The fact that the molecule is also involved in normal meiosis suggests an important correlation between the molecule, chromosomal replication, cell division, and the onset of oncogenesis.

DETAILED DESCRIPTION OF PREFERRED EMBODIMENTS

Example 1

Experiments were carried out to identify and to isolate cDNA corresponding to mRNA found exclusively in testis, and hence genes expressed only in testis cells. To do this, the methodology described by Diatchenko et al, Proc. Natl. Acad. Sci USA 93:6025–6030 (1996), incorporated by reference, was used to generate cDNA fragments specifically expressed in human testis cells, which had been obtained from biopsies of tumor free patients. Specifically, two mg of mRNA was taken from each of two, different testicular tissue specimens, and was used as a tester probe. Driver cDNA was obtained by synthesizing cDNA from mRNA taken from ten healthy tissue specimens (colon, stomach, brain, resting and activated peripheral blood mononuclear cells, skeletal muscle, liver, kidney, lungs and skin). Diatchenko, et al, supra, was followed to carry out suppression subtractive hybridization PCR, after tester and driver cDNA were permitted to hybridize. The resulting, isolated fragments were then used to isolate full length transcript. To do this, a cDNA phagemid library was constructed, using the same cDNA (i.e., the normal testis library), using 5 mg of mRNA. A library of $4\times10^6$ primary clones was produced and, following standard isolation procedures, the phagemid library was hybridized onto nitrocellulose membranes and then blotted with the fragments obtained previously. Following blotting, the membranes were washed, and any phagemids which had bound to immobilized cDNA were eluted. The eluted, full length molecules were used to prepare double stranded cDNA, using known methods, and the cDNA was then re-ligated into precut vectors, and then used for transfections and amplification. An expression library of 400,000 recombinants resulted.

Example 2

Following the creation of the expression library described supra, immune screening experiments were carried out to determine if any IgGs against the expression products of the library were present in serum from a tumor patient. To do this, a serum sample of a patient with renal cell cancer was diluted, 1:100, and then screened against 200,000 of the recombinants, following Türeci, et al, Cancer Res 56:4766–4772 (1996), U.S. Pat. No. 5,698,396 both of which are incorporated by reference. Reactive clones were visualized by incubation with an anti-human, Fc specific, alkaline phosphatase labelled antibody, which was then developed with the dye 5-bromo-4-chloro-3-indolyl phosphate, and nitroblue tetrazolium, following known methods. Of the 200,000 clones screened, five were positive. Three of these were found to be identical to part of a previously identified protein, i.e., SCP1, a protein whose expression has been linked, specifically to the meiotic prophase of spermatocytes, and which has been linked to the pairing of homologous chromosomes, which is essential to the generation of haploid cells in meioses I. The three positive clones were sequenced and found to correspond to nucleotides 726–2401, 147–2728, and 634–2462 of SCP1, but for changes at position 225 where CAT was replaced by TTT leading to F instead of H, and at position 226, glycine was replaced by glutamine (GGG was replaced by GAG). Other changes may also be present. The sequence of SCP1 is set forth as SEQ ID NO:1 and is found in Meuwissen et al., Genomics 37: 101–106 (1997) incorporated by reference.

Example 3

Experiments were then carried out to determine whether or not the SCP1 molecule was being expressed by normal tissues. This was determined via Northern blotting, and via RT-PCR. Northern blotting followed Chomczynsky, et al. Anal. Biochem 72:248–254 (1976), incorporated by reference. To elaborate, mRNA was removed from various tissue samples, checked for integrity via electrophoresis in formalin/MOPS gels, and then 10 mg from each sample were blotted onto nylon membranes, prehybridized, and then incubated with a $^{32}$P labelled cDNA probe which consisted of nucleotides 2715–3264 of SCP1 (SEQ ID No: 1). Specifically the probes were hybridized overnight at 42° C. in a solution of 50% formamide 6× SSC, 5× Denhardt's, and 0.2% SDS. Membranes were then washed at progressively higher stringencies, with the final wash at 1× SSC, 0.2% SDS at 65° C. Autoradiography was conducted at −70° C., for up to 7 days.

To carry out RT-PCR, total RNA was extracted, primed with an oligo-dT (18) nucleotide, and then reverse transcribed. Primers used were:

5'-GTACAGCAGA AAGCAAGCAA CTGAATG (SEQ ID NO: 2)
and
5'-GAAGGAACTG CTTTAGAATC CAATTTCC-3' (SEQ ID NO: 3).

The expected primer product size was 564 base pairs.

The only normal tissue sample to test positive was testis.

The RT-PCR protocol set forth supra was also used on tumor tissue samples. These results are set forth in the Table which follows. Northern blotting confirmed the work for renal, breast, and glioma tumor samples.

| Tumor Type | SCP1 Expression (positive/number tested) |
|---|---|
| melanoma | 4/28 |
| breast cancer | 9/33 |
| colorectal carcinoma | 0/32 |
| prostate cancer | 0/27 |
| glioma | 6/15 |
| gastric carcinoma | 1/10 |
| thyroid cancer | 0/5 |
| lymphoma or leukemia | 0/14 |
| lung carcinoma (NSCLC) non-small cell | 1/14 |
| renal cell carcinoma | 3/36 |
| ovarian carcinoma | 3/12 |
| seminoma | 0/2 |
| endometrial carcinoma | 0/8 |
| sarcoma | 0/4 |

Example 4

The analysis discussed, supra, was carried forward with Southern blotting, in accordance with Maniatis, et al, Molecular Cloning: A Laboratory Manual (Cold Spring Harbor Laboratory, 1982). In brief, the endonuclease Hae III was used on DNA extracted from testis and peripheral blood lymphocytes. Equal amounts of sample were checked by staining, visualized under UV light, and then were hybridized with full length cDNA for SCP1 at 6× SSC, 4× Denhardt's and 0.5% SDS, followed by washing and autoradiography as described above.

The banding patterns which resulted suggested a gene family, rather than a single gene.

Example 5

A final set of experiments was then carried out to test for presence of the SCP1 protein. This was done by Western blotting. SCP1 specific rabbit antiserum, described by Schmekel et al, Chromosoma 102: 682–692 (1993), incorporated by reference, was used. Cell lysates (10 ug, per lane), were mixed with 2× SDS sample buffer (0.1M Tris-HCl, pH 6.8, 0.2M dithiothreitol, 4% SDS, 0.2% bromophenol blue, 20% glycerol), electrophoresed on 12% SDS gels, via PAGE, and were then blotted to nylon membranes. The membranes were blocked with 5% non-fat milk in TBS for 1 hour, to address non-specific binding, and the membranes were then incubated with 1:100 diluted rabbit -anti SCP1 antiserum. The blots were then incubated for 1 hour with alkaline phosphatase conjugated anti-IgG. Membranes were washed extensively with TBS and 0.01% Tween, following each incubation. Positive reactions were monitored in the same fashion as is described, supra.

A 125 kDa protein was detected in lysates of normal testis cells and tumor cells, but in no other samples, indicating that SCP1 functions as a marker for tumor cells.

The foregoing examples demonstrate several features of the invention. These include diagnostic methods for determining presence of transformed cells, such as cancer cells, in a sample. The examples show that there is a family of SCP genes, such as SCP-1. Hence, the invention involves, inter alia, detecting an SCP protein or mRNA for an SCP gene in a sample taken from a source other than testis, wherein presence of either or both of these is indicative of a pathology, such as cancer or some other type of transformed cells. Exemplary of the type of diagnostic assays which can be carried out are amplification assays such as polymerase chain reaction, or immunoassays. It is especially preferred to assay for SCP-1, as a determination of breast cancer, ovarian cancer, renal cell carcinoma, or glioma.

The SCP proteins, as indicated, have been associated, exclusively, with meiosis. As a rule, cells other than germ cells do not undergo meiosis. Hence, the expression of SCP proteins such as SCP-1 in a context other than germ cells undergoing meiosis is clearly an indication of an abornmality. It is believed that expression of SCP proteins may contribute to the genetic instability of cancer cells, leading to abnormalities such as aneuploidy, manifesting the phenomenon in early neoplastic change. One aspect of the invention, then, is a method for determining presence of an abnormal condition by assaying for an SCP protein, or a peptide derived from the protein, wherein the presence of the protein at all, or an abnormal level of the protein (which may include its presence), is indicative of an abnormality, such as cancer. There are many ways to carry out this type of assay. For example, as indicated herein, antibodies to the protein were found in patient samples. One can assay for these antibodies using, e.g., the methodology described herein, or by using a purified SCP protein or antigenic fragment thereof, and so forth. One can also assay for the protein itself, using antibodies, which may be isolated from samples, or generated using an SCP protein and standard techniques. This antibodies can then be labelled, if desired, and used in standard immunoassays.

Similarly, any and all nucleic acid hybridization systems can be used, including amplification assays, such as PCR, basic probe hybridization assays, and so forth. The antibodies, such as polyclonal antibodies, monoclonal antibodies, the hybridomas which produce them, recombinantly produced antibodies, binding fragments of these, hybridization kits, DNA probes, and so forth, are all additional features of the invention.

Any of these assays can also be used in progression/regression studies. Since it is clear that a low or non-existent level of expression of SCP protein is found in normal cells, one can monitor the course of abnormality involving expression of SCP, simply by monitoring levels of the protein, its expression, and so forth using any or all of the methods set forth supra.

It should be clear that these methodologies may also be used to track the efficacy of a therapeutic regime. Essentially, one can take a baseline value for the SCP protein or proteins being tested, using any of the assays discussed supra, administer a given therapeutic agent, and then monitor levels of the protein thereafter, observing changes in SCP levels as indicia of the efficacy of the regime.

The identification of SCP proteins as being implicated in pathological conditions such as cancer also suggests a number of therapeutic approaches to such conditions. The experiments set forth supra establish that antibodies are produced in response to expression of the protein, suggesting its use as a vaccine. Hence, a further embodiment of the invention is the treatment of conditions which are characterized by aberrant or abnormal levels of one or more SCP proteins, via immunotherapeutic approaches. One of these approaches is the administration of an amount of an SCP protein, or an immunogenic peptide derived from the protein in an amount sufficient to provoke or augment an immune response. The protein or peptide may be combined with one or more of the known immune adjuvants, such as saponins, GM-CSF, interleukins, and so forth. If the peptides are too small to generate a sufficient antibody response, they can be coupled to the well known conjugates used to stimulate responses.

Similarly, the immunotherapeutic approaches include administering an amount of inhibiting antibodies sufficient to inhibit the SCP protein. These antibodies may be, e.g., antibodies produced via any of the standard approaches elaborated upon supra.

T cell responses may also be elicited by using peptides derived from the SCP proteins which then complex, non-covalently, with MHC molecules, thereby stimulating proliferation of cytolytic T cells against any such complexes in the subject. It is to be noted that the T cells may also be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response.

The therapeutic approaches may also include gene therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the well known BCG vaccine, and so forth.

An additional DNA based therapeutic approach is the use of a vector which comprises one or more nucleotide sequences, preferably a plurality of these, each of which encodes an immunoreactive peptide derived from the expressed proteins. One can combine these peptide expressing sequences in all possible variations, such as one from each protein, several from one or more protein and one from each of the additional proteins, a plurality from some and none from others, and so forth.

Also a feature of the invention are the mutein forms of SCP-1 and the nucleic acid molecule encoding it, as described supra. These muteins can be used in the same way SCP molecules can be used.

The invention also involves a method for determining substances produced by a subject capable of eliciting an immune response, wherein one produces a cDNA library of a normal cell taken from a subject, such as a testis cell, inserting the cDNA molecules of the library into an expression vector, transfecting the vector into host cells to produce transfected host cells and then culturing the transfected host cell to express the substance of interest. Following this, the cells are lysed to form a lysate, which is then contacted with a sample of a body fluid taken from a subject, which contains an immunologic binding partner for the immunoreactive substance. This step removes any immunologic binding partner from said sample which is specific for non-transfected host cells. The resulting sample is then contacted to a sample of lysed host cells transfected with the same vector which does not contain any library cDNA which removes any immunologic binding partners specific for vector produced antigens. Then, the sample is contacted to the lysate so that any binding partners specific substance bind thereto, after which one determines whether or not any binding partners have, in fact, bound to such substances, so as to determine said immunoreactive substance. This method is similar to that described in e.g., Ser. No. 08/580,980, now U.S. Pat. No. 5,698,396, except that the source of the library is a normal cell, such as a testis cell. As the examples, supra, indicate, this type of library was used to identify the tumor antigen. The body fluid sample may be taken from the same subject from whom the testis cells are taken (autologous serum), or it may be from a different individual. As in the Ser. No. 08/580,980 application, the cDNA so identified may be isolated, as can the binding partner. Relevant host cells for transformation may be eukaryotic, or prokaryotic, such as *E. coli*, and the expression vectors may be any of the standard expression vectors, such as a viral vector, a phage vector, and so forth. The sample used may be any of the sample types used in biological analysis, such as serum, blood cerebrospinal fluid, urine, stool samples, tissue samples such as skin, and so forth. Various types of antigens can be identified in this way, such as cancer associated antigens, autoimmune antigens, antigen associates with pathogens, such as viruses, and so forth. The methodology is conveniently carried out by, inter alia, immobilizing the lysate described supra to, e.g., a membrane, such as a nylon or a cellulose membrane.

Other features of the invention will be clear to the skilled artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for determining presence of a transformed cell, comprising assaying a sample of cells taken from tissue other than testis for expression of a member of the SCP gene family, wherein expression thereof is indicative of transformed cells in said sample.

2. The method of claim 1, wherein said member of the SCP gene family is SCP-1.

3. The method of claim 1, comprising determining an antibody specific for said member of the SCP gene family in said sample.

4. The method of claim 1, further comprising determining presence of mRNA for said member of the SCP gene family in said sample.

5. The method of claim 4, comprising determining presence of mRNA via polymerase chain reaction.

6. The method of claim 1, comprising assaying said sample for an SCP protein.

7. The method of claim 6, wherein said SCP protein is SCP-1.

8. The method of claim 6, comprising assaying said sample via an immunoassay.

9. The method of claim 1, wherein said transformed cell is a cancer cell.

10. The method of claim 9, wherein said cancer cell is a renal cancer cell, a glioma, an ovarian cancer cell, or a breast cancer cell.

11. A method for following progress of a therapeutic regime designed to alleviate a condition characterized by abnormal expression of an SCP protein, comprising:

(a) assaying a sample from a subject to determine level of a parameter selected from the group consisting of (i) a peptide derived from said SCP protein, (ii) a cytolytic T cell specific for cells presenting said peptide, and (iii) an antibody which specifically binds to said peptide of said SCP protein, at a first time point;

(b) assaying level of the parameter selected in (a) at a second point in time and comparing it to the level determined in (a) as a determination of effect of said therapeutic regime.

12. Method for determining regression, progression or onset of cancer comprising monitoring a sample from a patient with cancer for a parameter selected from the group consisting of (i) an SCP protein, (ii) a peptide derived from an SCP protein and (iii) cytolytic T cells specific for a peptide derived from an SCP protein and an MHC molecule to which it is bound and is indicative of progression or regression or onset of cancer.

13. The method of claim 12, wherein said sample is a body fluid.

14. The method of claim 12, wherein said sample is a tissue.

15. The method of claim 12, wherein contacting said sample with an antibody which specifically binds with an SCP protein or peptide.

16. The method of claim 15, wherein said antibody is labelled with a radioactive label or an enzyme.

17. The method of claim 15, wherein said antibody is a monoclonal antibody.

18. The method of claim 12, comprising amplifying RNA which codes for an SCP protein.

19. The method of claim 18, wherein said amplifying comprises carrying out polymerase chain reaction.

20. The method of claim 12, comprising contacting said sample with a nucleic acid molecule which specifically hybridizes to a nucleic acid molecule which codes for or expresses an SCP protein.

21. The method of claim 12, comprising assaying said sample for said peptide.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 3393 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
GCCCTCATAG  ACCGTTTGTT  GTAGTTCGCG  TGGGAACAGC  AACCCACGGT  TTCCCGATAG       60

TTCTTCAAAG  ATATTTACAA  CCGTAACAGA  GAAATGGAA   AAGCAAAAGC  CCTTTGCATT      120

GTTCGTACCA  CCGAGATCAA  GCAGCAGTCA  GGTGTCTGCG  GTGAAACCTC  AGACCCTGGG      180

AGGCGATTCC  ACTTTCTTCA  AGAGTTTCAA  CAAATGTACT  GAAGATGATT  TGGAGTTTCC      240

ATTTGCAAAG  ACTAATCTCT  CCAAAAATGG  GGAAAACATT  GATTCAGATC  CTGCTTTACA      300

AAAAGTTAAT  TTCTTGCCCG  TGCTTGAGCA  GGTTGGTAAT  TCTGACTGTC  ACTATCAGGA      360

AGGACTAAAA  GACTCTGATT  TGGAGAATTC  AGAGGGATTG  AGCAGAGTGT  TTTCAAAACT      420

GTATAAGGAG  GCTGAAAAGA  TAAAAAAATG  GAAAGTAAGT  ACAGAAGCTG  AACTGAGACA      480

GAAAGAAAGT  AAGTTGCAAG  AAAACAGAAA  GATAATTGAA  GCACAGCGAA  AAGCCATTCA      540

GGAACTGCAA  TTTGGAAATG  AAAAGTAAG   TTTGAAATTA  GAAGAAGGAA  TACAAGAAAA      600

TAAAGATTTA  ATAAAAGAGA  ATAATGCCAC  AAGGCATTTA  TGTAATCTAC  TCAAAGAAAC      660

CTGTGCTAGA  TCTGCAGAAA  AGACAAGAA   ATATGAATAT  GAACGGGAAG  AAACCAGGCA      720

AGTTTATATG  GATCTAAATA  ATAACATTGA  GAAAATGATA  ACAGCTCATG  GGGAACTTCG      780

TGTGCAAGCT  GAGAATTCCA  GACTGGAAAT  GCATTTTAAG  TTAAGGAAG   ATTATGAAAA      840

AATCCAACAC  CTTGAACAAG  AATACAAGAA  GGAAATAAAT  GACAAGGAAA  AGCAGGTATC      900

ACTACTATTG  ATCCAAATCA  CTGAGAAAGA  AAATAAAATG  AAAGATTTAA  CATTTCTGCT      960

AGAGGAATCC  AGAGATAAAG  TTAATCAATT  AGAGGAAAAG  ACAAAATTAC  AGAGTGAAAA     1020

CTTAAAACAA  TCAATTGAGA  AACAGCATCA  TTTGACTAAA  GAACTAGAAG  ATATTAAAGT     1080

GTCATTACAA  AGAAGTGTGA  GTACTCAAAA  GGCTTTAGAG  GAAGATTTAC  AGATAGCAAC     1140

AAAAACAATT  TGTCAGCTAA  CTGAAGAAAA  AGAAACTCAA  ATGGAAGAAT  CTAATAAAGC     1200

TAGAGCTGCT  CATTCGTTTG  TGGTTACTGA  ATTTGAAACT  ACTGTCTGCA  GCTTGGAAGA     1260

ATTATTGAGA  ACAGAACAGC  AAAGATTGGA  AAAAAATGAA  GATCAATTGA  AAATACTTAC     1320

CATGGAGCTT  CAAAAGAAAT  CAAGTGAGCT  GGAAGAGATG  ACTAAGCTTA  CAAATAACAA     1380

AGAAGTAGAA  CTTGAAGAAT  TGAAAAAAGT  CTTGGGAGAA  AAGGAAACAC  TTTTATATGA     1440

AAATAAACAA  TTTGAGAAGA  TTGCTGAAGA  ATTAAAAGGA  ACAGAACAAG  AACTAATTGG     1500

TCTTCTCCAA  GCCAGAGAGA  AAGAAGTACA  TGATTTGGAA  ATACAGTTAA  CTGCCATTAC     1560

CACAAGTGAA  CAGTATTATT  CAAAAGAGGT  TAAAGATCTA  AAAACTGAGC  TTGAAAACGA     1620

GAAGCTTAAG  AATACTGAAT  TAACTTCACA  CTGCAACAAG  CTTTCACTAG  AAAACAAAGA     1680

GCTCACACAG  GAAACAAGTG  ATATGACCCT  AGAACTCAAG  AATCAGCAAG  AAGATATTAA     1740

TAATAACAAA  AAGCAAGAAG  AAAGGATGTT  GAAACAAATA  GAAAATCTTC  AAGAAACAGA     1800

AACCCAATTA  AGAAATGAAC  TAGAATATGT  GAGAGAAGAG  CTAAAACAGA  AAGAGATGA      1860
```

| | | | | | | |
|---|---|---|---|---|---|---|
| AGTTAAATGT | AAATTGGACA | AGAGTGAAGA | AAATTGTAAC | AATTTAAGGA | AACAAGTTGA | 1920 |
| AAATAAAAAC | AAGTATATTG | AAGAACTTCA | GCAGGAGAAT | AAGGCCTTGA | AAAAAAAAGG | 1980 |
| TACAGCAGAA | AGCAAGCAAC | TGAATGTTTA | TGAGATAAAG | GTCAATAAAT | TAGAGTTAGA | 2040 |
| ACTAGAAAGT | GCCAAACAGA | AATTTGGAGA | AATCACAGAC | ACCTATCAGA | AAGAAATTGA | 2100 |
| GGACAAAAAG | ATATCAGAAG | AAAATCTTTT | GGAAGAGGTT | GAGAAAGCAA | AAGTAATAGC | 2160 |
| TGATGAAGCA | GTAAAATTAC | AGAAGAAAT | TGATAAGCGA | TGTCAACATA | AAATAGCTGA | 2220 |
| AATGGTAGCA | CTTATGGAAA | AACATAAGCA | CCAATATGAT | AAGATCATTG | AAGAAAGAGA | 2280 |
| CTCAGAATTA | GGACTTTATA | AGAGCAAAGA | ACAAGAACAG | TCATCACTGA | GAGCATCTTT | 2340 |
| GGAGATTGAA | CTATCCAATC | TCAAAGCTGA | ACTTTTGTCT | GTTAAGAAGC | AACTTGAAAT | 2400 |
| AGAAAGAGAA | GAGAAGGAAA | AACTCAAAAG | AGAGGCAAAA | GAAAACACAG | CTACTCTTAA | 2460 |
| AGAAAAAAAA | GACAAGAAAA | CACAAACATT | TTTATTGGAA | ACACCTGAAA | TTTATTGGAA | 2520 |
| ATTGGATTCT | AAAGCAGTTC | CTTCACAAAC | TGTATCTCGA | AATTTCACAT | CAGTTGATCA | 2580 |
| TGGCATATCC | AAAGATAAAA | GAGACTATCT | GTGGACATCT | GCCAAAAATA | CTTTATCTAC | 2640 |
| ACCATTGCCA | AAGGCATATA | CAGTGAAGAC | ACCAACAAAA | CCAAAACTAC | AGCAAAGAGA | 2700 |
| AAACTTGAAT | ATACCCATTG | AAGAAAGTAA | AAAAAGAGA | AAAATGGCCT | TTGAATTTGA | 2760 |
| TATTAATTCA | GATAGTTCAG | AAACTACTGA | TCTTTTGAGC | ATGGTTCAG | AAGAAGAGAC | 2820 |
| ATTGAAAACA | CTGTATAGGA | ACAATAATCC | ACCAGCTTCT | CATCTTTGTG | TCAAAACACC | 2880 |
| AAAAAAGGCC | CCTTCATCTC | TAACAACCCC | TGGACCTACA | CTGAAGTTTG | GAGCTATAAG | 2940 |
| AAAAATGCGG | GAGGACCGTT | GGGCTGTAAT | TGCTAAAATG | GATAGAAAAA | AAAAACTAAA | 3000 |
| AGAAGCTGAA | AAGTTATTTG | TTTAATTTCA | GAGAATCAGT | GTAGTTAAGG | AGCCAATAA | 3060 |
| CGTGAAACTT | ATAGTTAATA | TTTTGTTCTT | ATTTGCCAGA | GCCACATTTT | ATCTGGAAGT | 3120 |
| TGAGACTTAA | AAAATACTTG | CATGAATGAT | TTGTGTTTCT | TTATATTTTT | AGCCTAAATG | 3180 |
| TTAACTACAT | ATTGTCTGGA | AACCTGTCAT | TGTATTCAGA | TAATTAGATG | ATTATATATT | 3240 |
| GTTGTTACTT | TTTCTTGTAT | TCATGAAAAC | TGTTTTTACT | AAGTTTCAA | ATTTGTAAAG | 3300 |
| TTAGCCTTTG | AATGCTAGGA | ATGCATTATT | GAGGGTCATT | CTTTATTCTT | TACTATTAAA | 3360 |
| ATATTTTGGA | TGCAAAAAAA | AAAAAAAAAA | AAA | | | 3393 |

( 2 ) INFORMATION FOR SEQ ID NO: 2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

| | | | |
|---|---|---|---|
| GTACAGCAGA | AAGCAAGCAA | CTGAATG | 27 |

( 2 ) INFORMATION FOR SEQ ID NO: 3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

| | | | |
|---|---|---|---|
| GAAGGAACTG | CTTTAGAATC | CAATTTCC | 28 |